United States Patent
Sun et al.

(10) Patent No.: US 9,795,340 B2
(45) Date of Patent: Oct. 24, 2017

(54) VACUUM-PUMP SUCKER

(75) Inventors: Chi-Kuang Sun, Taipei (TW); Szu-Yu Chen, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 104 days.

(21) Appl. No.: 12/966,218

(22) Filed: Dec. 13, 2010

(65) Prior Publication Data
US 2012/0150042 A1 Jun. 14, 2012

(51) Int. Cl.
*A61B 5/00* (2006.01)

(52) U.S. Cl.
CPC .......... *A61B 5/6834* (2013.01); *A61B 5/0059* (2013.01); *A61B 5/6882* (2013.01)

(58) Field of Classification Search
CPC .... A61B 5/0059; A61B 5/6834; A61B 5/6882
See application file for complete search history.

(56) References Cited

U.S. PATENT DOCUMENTS

| | | | |
|---|---|---|---|
| 5,788,639 A * | 8/1998 | Zavislan et al. | 600/476 |
| 2002/0154399 A1* | 10/2002 | Eastman et al. | 359/398 |
| 2005/0171441 A1* | 8/2005 | Zavislan | 600/476 |
| 2005/0200129 A1* | 9/2005 | Bongiorno | F16L 23/02 |
| | | | 285/364 |

FOREIGN PATENT DOCUMENTS

| | | |
|---|---|---|
| JP | 2005307971 A | 11/2005 |
| JP | 2009004610 A | 1/2009 |

* cited by examiner

*Primary Examiner* — Ruth S Smith
(74) *Attorney, Agent, or Firm* — Hannah M. Tien

(57) ABSTRACT

This invention relates to a vacuum-pump sucker for high-resolution microscopy comprising a sucker body and a transparent plate. The vacuum-pump sucker is designed as a stabilizer for sample stabilization in a clinical optical virtual biopsy system with sub-micron resolution. The sucker is connected with a vacuum pump. As the vacuum pump pumps out air or gas, tissues around the imaged area will be sucked by the sucker and the distance between objective lens and the imaged tissue can be stabilized. In this way, the stability and resolution of the clinical biopsy system can be greatly improved.

5 Claims, 6 Drawing Sheets

VACUUM-PUMP SUCKER

FIELD OF THE INVENTION

The present invention relates to a vacuum-pump sucker for a microscopy, particular to a vacuum-pump sucker for sample stabilization in a clinical optical virtual biopsy system with sub-micron resolution.

BACKGROUND OF THE INVENTION

In the prior arts, a stabilizer device for confocal microscopy is either glued to human tissues with biogel-based adhesive or with a syringe pump for sucking water. However, the biogel-based adhesive may easily lead to physical damage or bio-effects, such as irritation. It is not suitable for internal tissues. As to syringe pump, a depth control of a focus lens can not be performed independently. In contrast, a vacuum-pump sucker of the present invention has no bio-toxicity while damages to human tissues during observation can be avoided, and thus the vacuum-pump sucker of the present invention is more suitable for investigating internal tissues. In comparison with the syringe pump systems, the sucker system of the present invention is much easier to control the depth of the images.

BRIEF DESCRIPTIONS OF THE DRAWINGS

SUMMARY OF THE INVENTION

The present invention provides a vacuum-pump sucker for a microscopy comprising:
a sucker body having an imaging window for an imaging light passing through a focusing lens, and having a channel for sucking a tissue of a user connected to a vacuum pump.

According to the present invention, the vacuum-pump sucker further comprises a transparent plate for covering and connected to the imaging window.

According to the present invention, preferably the suck body can removably receive or retrieve the focusing lens.

According to the present invention, preferably the transparent plate is a glass plate or a plastic plate.

According to the present invention, preferably the focusing lens is a Grinrod, a aspherical lens or a objective lens.

The problems to be solved in the present invention are the problems of insufficient stability encountered in a clinical application of well-known prior arts, a biogel-based adhesive is used to fix a microscopy onto human tissues, or a syringe pump is used to pump water to absorb and fix the human tissues. The present invention solves the problems encountered, such as a bio-toxicity of the biogel-based adhesive, an easy flowing-away of water when an observation direction of the objective lens is changed, uneasy control of a depth of images. After the problems are solved in the present invention, the sub-micron microscopy can be applied to investigate internal tissues or mucosa tissues, and the image depth can be accurately controlled to obtain living tissue images of 3D.

The technical means of the present invention is to use vacuum pump of air to suck or absorb tissues to be fixed. The tissues to be sucked are the observed tissues at the observing zone. The focusing lens can be independently moved against the observed tissues and the user observes the tissues via an imaging window at the center of the sucker.

The effects of the present invention are as follows: Air or gas is used in the present invention as sucked fluid. The air or gas will not render any bio-toxic and the conventional flowing-away of sucked fluid will not happen. The use of air or gas can improve the bio-toxicity problem by using a sub-micron microscopy, and an observation direction is changed in order to solve the problem of conventional flowing-away of sucked fluid. Furthermore, a relative location between the focusing lens and the observed tissues is changed to regulate a position and direction of observation and a depth of images. A control of retrieval of images is more convenient and accurate. A scanning of a large range tissue and living images of 3D in clinical application can be achieved.

DETAILED DESCRIPTION OF THE INVENTION

Figure 1:
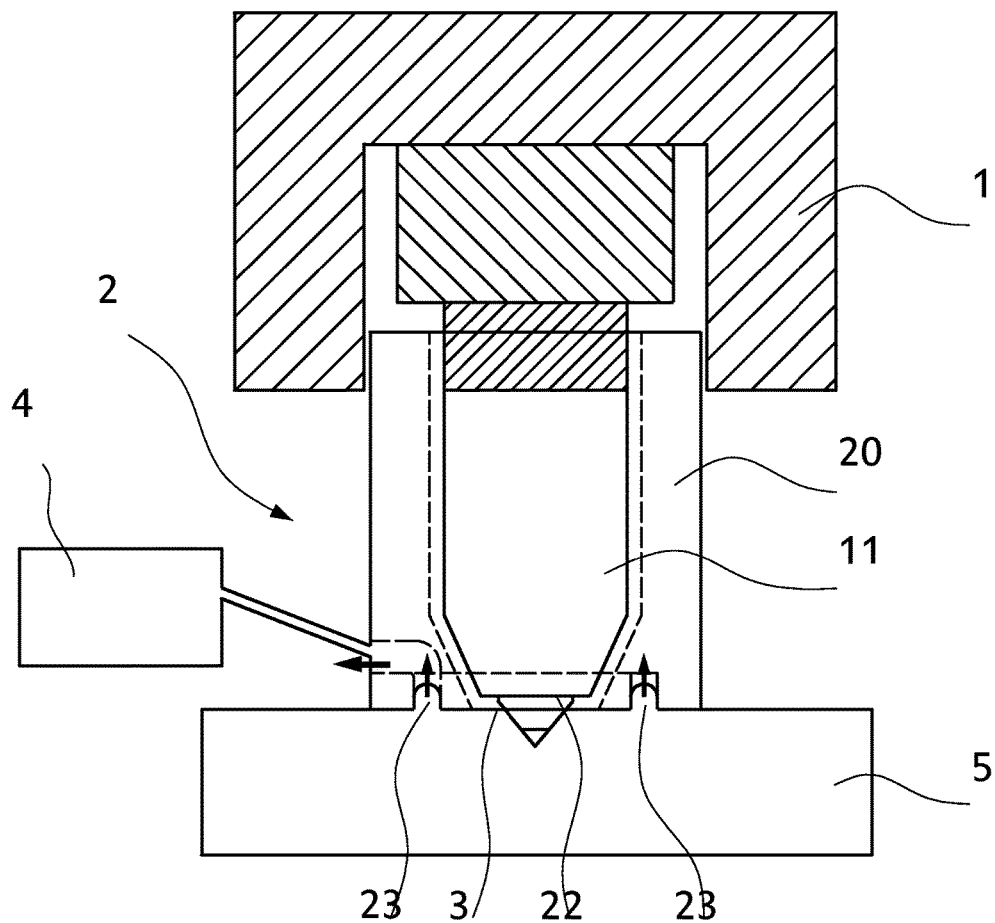
FIG. 1 is a schematic view of the vacuum-pump sucker of the first embodiment of the present invention.
Figure 2:
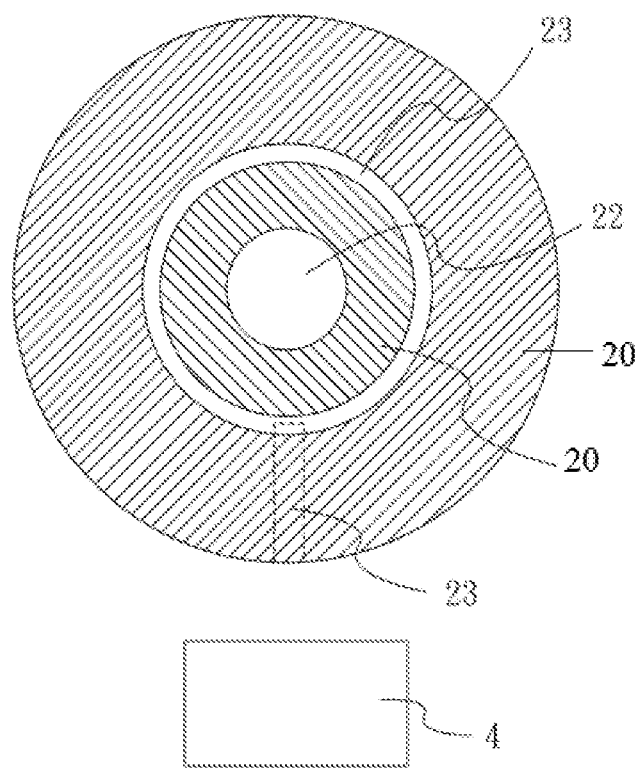
FIG. 2 is a side view of the vacuum-pump sucker of FIG. 1 of the present invention.

Please refer to FIG. 1 which is a schematic view of the vacuum-pump sucker of the present invention. FIG. 2 is a side view of the vacuum-pump sucker of FIG. 1 of the present invention. The vacuum-pump sucker 2 comprises a sucker body 20 and a glass plate 3. A focusing lens 11 which is connected to an imaging system 1 can be removably inserted into the sucker body 20. The design specifications of the vacuum-pump sucker 2 are as follows: (1) The sucker 2 must be fixed onto a main body of the imaging system 1. Please refer to FIG. 1 which is a first embodiment of the present invention. (2) The sucker 2 can independently move against a focusing lens 11. Please refer to FIG. 1. (3) There is an imaging window 22 at the center of contact surface between the sucker 2 and human tissues 5 for exciting light and excited light transmitting through. The exciting light and excited light also pass through the glass plate 3. A circle of channel 23 for vacuum sucking tissues 5 is disposed at the circumference of the imaging window 22. The channel 23 is connected to a vacuum pump 4 for pumping gas. Please refer to FIGS. 1 and 2. (4) According to the species of imaging system 1, focusing lens 11 and different application demands, the size and shape of the imaging window 22 and the channel 23 can be revised and modified. The glass plate 3 is used to protect the focusing lens 11 from contamination. The sucker body 20 can be made from plastics, rubber, metal or alloy, etc. so that the sucker body 20 can be or can not be flexible.

Figure 3:
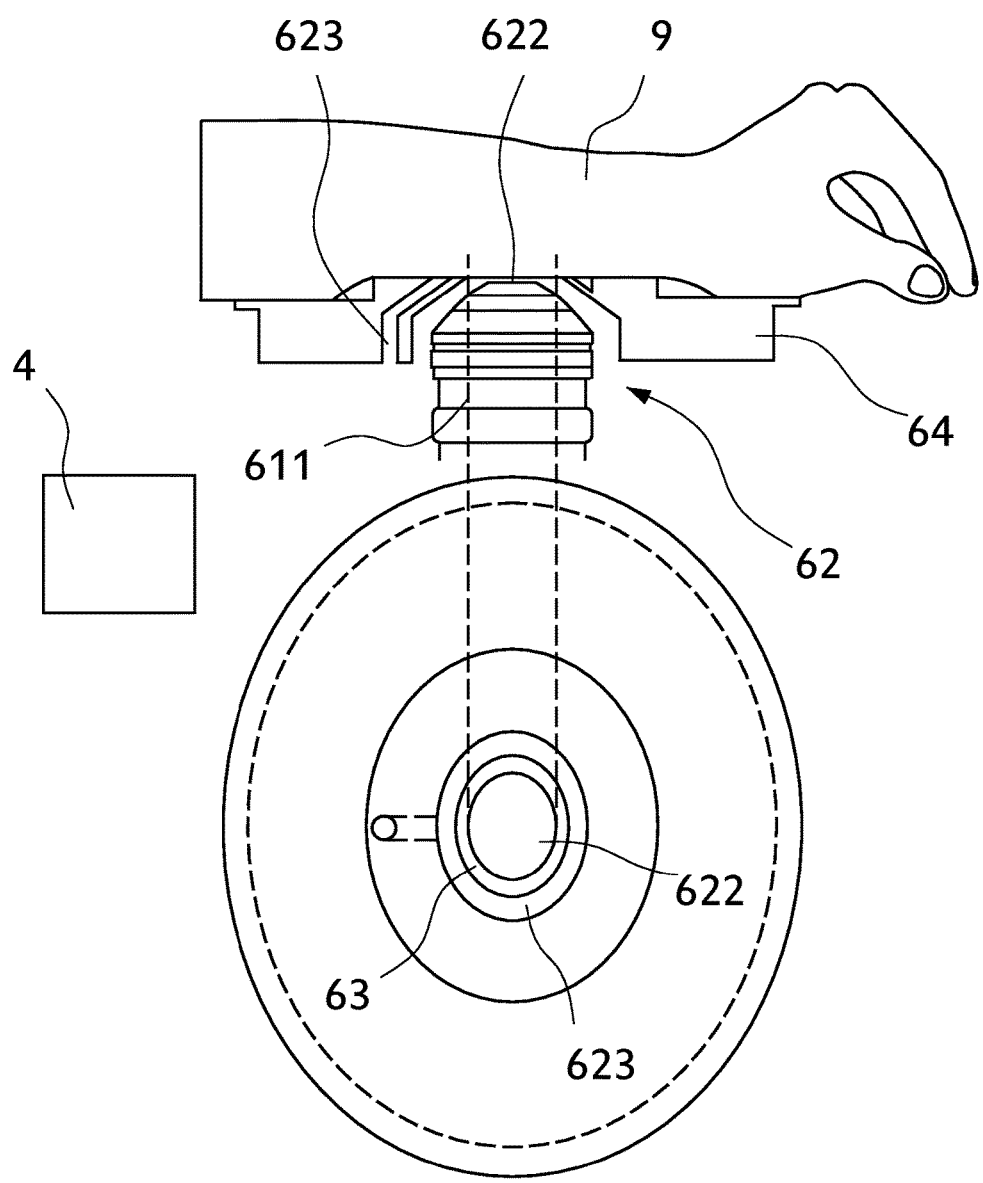
FIG. 3 is a second embodiment of the sucker of the present invention.

Please refer to FIG. 3 which is second embodiment of the present invention. In FIG. 3, a hand 9 is placed on the platform 64 and the objective lens 611 and is sucked by the sucker 62. A channel 623 and imaging window 622 are arranged in the sucker 62. A glass plate 63 is disposed above the imaging window 622 and contacts with the skin of the hand 9 of a user. An imaging system (not shown) is arranged and connected to the objective lens 611.

Figure 4A:
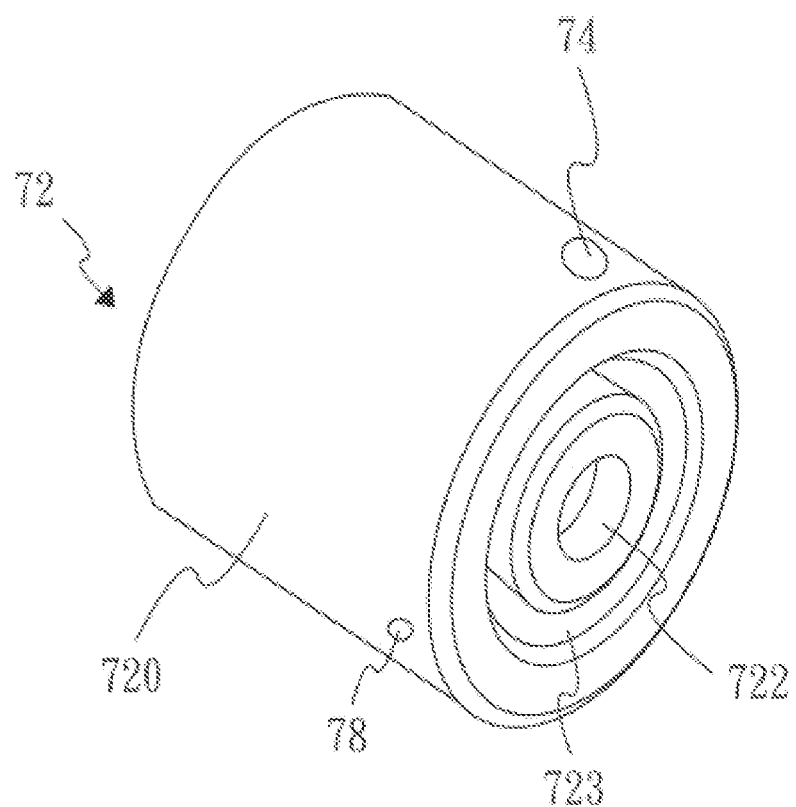
FIGS. 4A-4C are drawings of a rotary sucker of the third embodiment of the present invention.
Figure 4B:
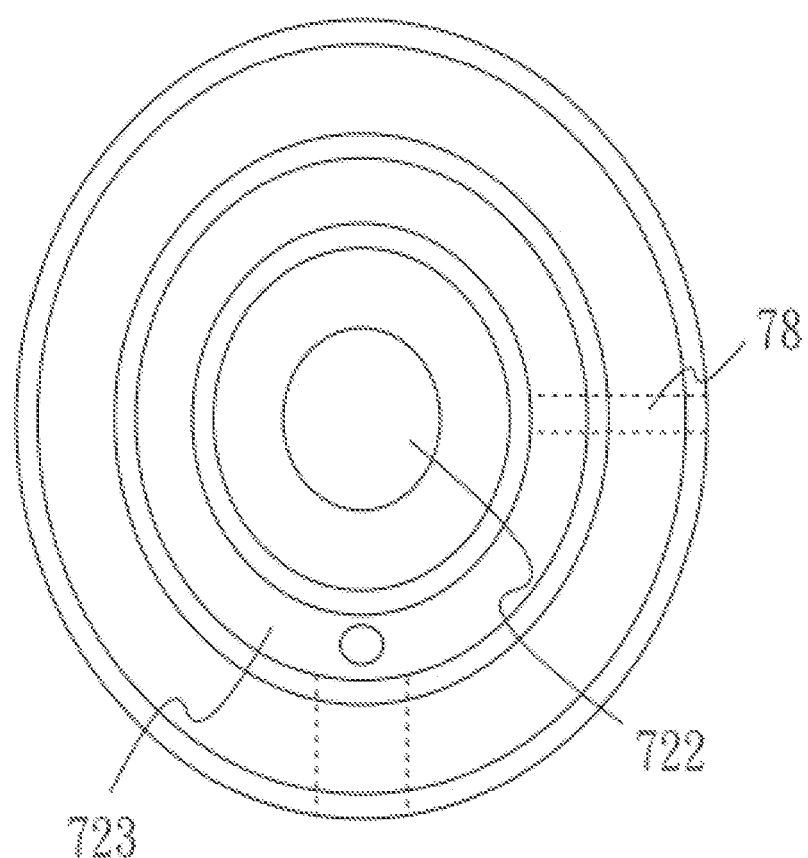
Figure 4C:
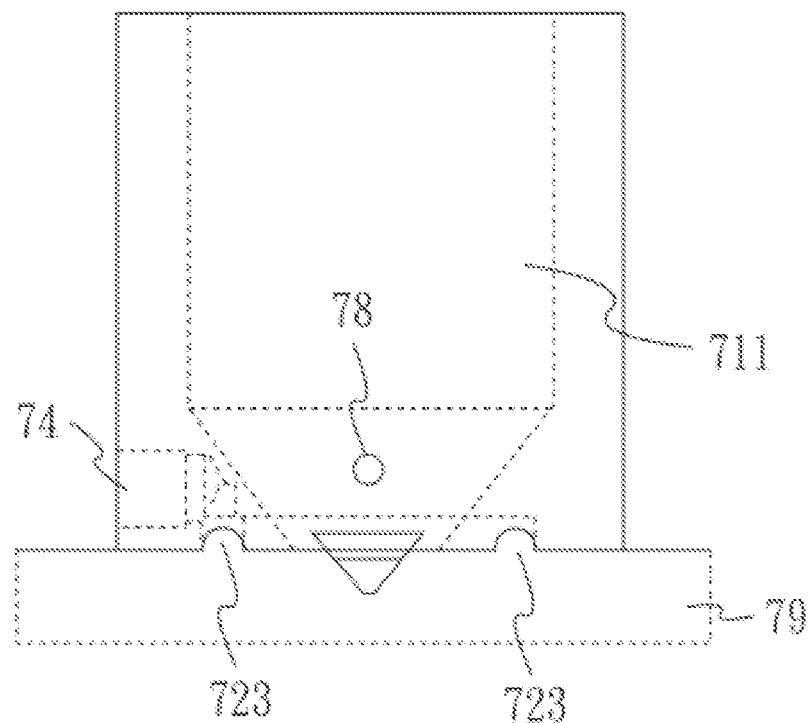

Please refer to FIGS. 4A-4C which are drawings of rotary sucker 72 of the third embodiment of the present invention. The rotary sucker 72 has an imaging window 722 and a sucker body 720. A channel 723 is disposed front of the sucker body 720. A vacuum pump hole 74 for connecting to a sucking pump is disposed on the sucker body 720. A media injection spot 78 for injecting oil-media or water-media is disposed on the sucker body 720. A glass plate can be inserted between the human skin 79 and the imaging window 722. During operation, a media is injected into the media injection spot 78. Because the objective lens can be oil objective lens or water objective lens, an oil-media or water-media are injected into respectively. Under the status of sucking, a media is injected between the objective lens 711 and the human skin 79. Then, the pump turns on to suck into vacuum state. The sucked region (such as a channel zone) and the imaging region (such as an imaging window zone) are dislocated (different regions) so that adding water, oil and moving the pump lens will not affect the stability of the stabilizer.

What is claimed is:

1. A vacuum-pump sucker to stabilize a tissue of a subject for an imaging system of a microscopy device having a focusing lens which is movable for changing observation direction and depth of images, comprising
    a sucker body, wherein
    (1) the sucker body allows the focusing lens to be removably inserted into the sucker body in order for the focusing lens to be independently moved within the sucker body for changing observation direction and depth of images,
    (2) one end of the sucker body is adapted to fix the vacuum-pump sucker onto a main body of the imaging system of the microscopy device,
    (3) another end of the sucker body provides a contact surface facing or contacting the tissue of the subject, and
    (4) the sucker body comprises a rigid material;
    a single vacuum pump;
    an imaging window positioned at the center of the contact surface of the sucker body to define an imaging window zone which is not connected with the single vacuum pump, wherein the imaging window allows an imaging light to pass through the focusing lens onto the tissue and the tissue to be observed via the imaging window; and
    a ring-shaped channel positioned at the circumference of the imaging window to define a channel zone, wherein the ring-shaped channel is connected with the single vacuum pump to create a suction only in the channel zone and to pump gas or liquid out of the channel zone;
    wherein the channel zone and the imaging window zone are dislocated and separated by a barrier to allow the suction to be created by the vacuum pump only in the channel zone, not in the imaging window zone so that only gas or liquid in the channel zone is pumped out and only the tissue of the subject in the channel zone is sucked, thereby stabilizing the tissue in the imaging window zone.

2. The vacuum-pump sucker of claim 1, further comprising a transparent plate covering the imaging window for protecting the focusing lens from contamination.

3. The vacuum-pump sucker of claim 2, wherein the transparent plate is a glass plate or a plastic plate.

4. The vacuum-pump sucker of claim 1, wherein the sucker body further comprises a media injection spot for injecting oil media or water-media.

5. The vacuum-pump sucker of claim 1, wherein the sucker body comprises metal or alloy.

* * * * *